(12) United States Patent
Kozlowski et al.

(10) Patent No.: US 7,872,082 B2
(45) Date of Patent: Jan. 18, 2011

(54) METHOD FOR PREPARING POLYMER MALEIMIDES

(75) Inventors: Antoni Kozlowski, Huntsville, AL (US); John Handley, Duluth, MN (US); Anthony G. Schaefer, Huntsville, AL (US); Brian Bray, Huntsville, AL (US); Ryan Odom, Huntsville, AL (US); Tony L. Sander, Madison, AL (US)

(73) Assignee: Nektar Therapeutics, San Carlos, CA (US)

( * ) Notice: Subject to any disclaimer, the term of this patent is extended or adjusted under 35 U.S.C. 154(b) by 476 days.

(21) Appl. No.: 11/490,268

(22) Filed: Jul. 19, 2006

(65) Prior Publication Data

US 2007/0049688 A1    Mar. 1, 2007

Related U.S. Application Data

(60) Provisional application No. 60/700,972, filed on Jul. 19, 2005.

(51) Int. Cl.
*C08F 22/40*    (2006.01)

(52) U.S. Cl. .................. 526/262; 526/215; 526/208; 526/333; 525/55

(58) Field of Classification Search ................ 526/262, 526/215, 208, 333; 525/55
See application file for complete search history.

(56) References Cited

U.S. PATENT DOCUMENTS

| | | | |
|---|---|---|---|
| 4,179,337 A | 12/1979 | Davis et al. | |
| 4,675,414 A | 6/1987 | DeFusco et al. | |
| 4,761,460 A | 8/1988 | Otsuka et al. | |
| 4,775,729 A | 10/1988 | DeFusco et al. | |
| 5,036,111 A | 7/1991 | Senneron et al. | |
| 5,053,423 A | 10/1991 | Liu | |
| 5,166,322 A | 11/1992 | Shaw et al. | |
| 5,585,484 A | 12/1996 | Acharya et al. | |
| 5,629,384 A | 5/1997 | Veronese et al. | |
| 5,641,856 A | 6/1997 | Meurs | |
| 5,648,506 A | 7/1997 | Desai et al. | |
| 5,766,897 A | 6/1998 | Braxton | |
| 5,844,020 A | 12/1998 | Paine et al. | |
| 5,922,675 A | 7/1999 | Baker et al. | |
| 5,932,462 A | 8/1999 | Harris et al. | |
| 5,977,163 A | 11/1999 | Li et al. | |
| 5,990,237 A | 11/1999 | Bentley et al. | |
| 6,180,134 B1 | 1/2001 | Zalipsky et al. | |
| 6,180,598 B1 | 1/2001 | Nelson | |
| 6,183,738 B1 | 2/2001 | Clark | |
| 6,303,119 B1 | 10/2001 | Weisgerber et al. | |
| 6,362,254 B2 | 3/2002 | Harris et al. | |
| 6,403,753 B1 | 6/2002 | Loy et al. | |
| 6,602,498 B2 * | 8/2003 | Shen | 424/78.08 |
| 6,673,905 B2 | 1/2004 | Pozsgay | |
| 6,828,401 B2 | 12/2004 | Nho et al. | |
| 6,875,841 B2 | 4/2005 | Sakanoue et al. | |
| 7,432,330 B2 * | 10/2008 | Kozlowski et al. | 525/343 |
| 2001/0044526 A1 | 11/2001 | Shen | |
| 2002/0082345 A1 | 6/2002 | Kozlowski et al. | |
| 2003/0065134 A1 | 4/2003 | Sakanoue et al. | |
| 2003/0162693 A1 | 8/2003 | Winslow et al. | |
| 2003/0170474 A1 | 9/2003 | Oiao et al. | |
| 2004/0109841 A1 * | 6/2004 | Shen | 424/78.23 |
| 2004/0110822 A1 | 6/2004 | McCluskey et al. | |
| 2004/0115165 A1 | 6/2004 | Rosen et al. | |
| 2004/0167287 A1 | 8/2004 | Kozlowski et al. | |

FOREIGN PATENT DOCUMENTS

| | | |
|---|---|---|
| EP | 1 283 233 A1 | 2/2003 |
| FR | 2 031 538 | 11/1970 |
| JP | 02 268155 | 11/1990 |
| JP | 03 012414 | 1/1991 |
| WO | 01/68601 | 9/2001 |
| WO | 01/84234 | 11/2001 |
| WO | 2004/060965 A2 | 7/2004 |
| WO | 2005/056636 A2 | 6/2005 |

OTHER PUBLICATIONS

Baldwin, et al., "Diastereoselective Diels-Alder Reactions between Substituted 1,3-Butadienes and N-α-Methylbenzylmaleimide", Tetrahedron Letters, 32(42):5877-5880 (1991).

Booth, et al., "Efficient recognition-induced accerleration of a [3+2] dipolar cycloaddition reaction", Tetrahedron Letters, 39:6987-6990, (1998).

Bravo, et al., "Synthesis of Polycyclic Systems Via Diels-Alder Reactions of Sugar Derived Dienes", Heterocycles, 53(1):81-92, (2000).

Brewer, et al., "Evidence for Possible Nonspecific Reactions between N-Ethylmaleimide and Proteins[1]", Analytical Biochemistry, 18:248-255, (1967).

Chujo, et al. "Reversible Gelation of Polyoxazoline by Means of Diels-Alder Reaction[1]", 23(10):2636-2641, (1990).

Enzon Pharmaceuticals, Macromolecular Engineering Technologies, pp. 1-14, (2004).

Gorin, et al., "Kinetics of the Reaction of N-Ethylmaleimide with Cysteine and Some Congeners", Archives of Biochemistry and Biophysics, 115:593-597, (1966).

(Continued)

*Primary Examiner*—Kamal A Saeed
*Assistant Examiner*—Valerie Rodriguez-Garcia
(74) *Attorney, Agent, or Firm*—Mark A. Wilson

(57) ABSTRACT

Methods for preparing polymeric reagents bearing a maleimide are provided. Also provided are compositions comprising the polymeric reagents, and conjugates prepared by polymeric reagents obtained by the described methods.

23 Claims, No Drawings

OTHER PUBLICATIONS

Grigg, et al., "X=Y-ZH Systems as Potential 1,3-Dipoles. Part 11. [1]Stereochemistry of 1,3-Dipoles by the Decarboxylative Route to Azomethine Ylides", J. Chem. Soc. Perkin Trans. I, pp. 2693-2701, (1998).

Harris, et al., "Poly(ethylene glycol) Chemistry and Biological Applications", ACS Symposium Series, ACS, Washinton D.C., (1997).

Konopíková, et al., "Synthesis and Fungicidal Activity of Isoazolines Fused", Collect. Czech. Chem. Commun. 57:1521-1536, (1992).

Luo, et al., "Highly Efficient and Thermally Stable Electro-optic Polymer from a Smartly Controlled Crosslinking Process", 15(19):1635-1638, (2003).

Nektar™—Transforming Therapeutics, Nektar Molecule Engineering: Polyethylene Glycol and Derivatives for Advanced PEGylation, pp. 1-20, (Catalog—2003).

Nektar™—Transforming Therapeutics, Nektar Advanced PEGylation: Polyethylene Glycol and Derivatives for Advanced PEGylation, pp. 1-24, (Catalog—2004).

NOF Corporation, "PEG Derivatives, Phospholipid and Drug Delivery Materials for Pharmaceuticals", pp. 1-46, (Catalogue 2003-1st).

NOF Corporation, "PEG Derivatives, Phospholipid and Drug Delivery Materials for Pharmaceuticals", pp. 1-50, (Catalogue 2003-2nd).

NOF Corporation, "PEG Derivatives, Phospholipids and Drug Delivery Materials for Pharmaceutical Products and Formulations", pp. 1-59, (Catalogue Ver. 8—Apr. 2006).

Partis, et al., "Cross-Linking of Protein by ω-Maleimido Alkanoyl N-Hydroxysuccinimido Esters", J. of Protein Chem., 2(3):263-277, (1983).

Philp, et al., "Recognition-induced control of a Diels-Alder reaction", Chem. Commu., pp. 879-880, (1998).

Polypure, Products; PEG amines; PEG acids and amino acids; PEG thiols and disulfides; BIOTINS, (Apr. 2004).

Polypure, Products; PEG amines; PEG acids and amino acids; PEG thiols and disulfides; BIOTINS, (Apr. 2005).

Quanta Biodesign, Labeling, Derivatization and Crosslinking Reagents for Biological and Related Materials with dPEG™, pp. 1-38, (Mar. 12, 2004).

Quanta Biodesign, Labeling, Modification and Crosslinking Reagents incorporating our unique monodispersed dPEG™ Technology, pp. 1-31, (Nov. 5, 2004).

Quanta Biodesign, Ltd., Leading innovator, producer and provider of monodisperse discrete PEG™ (dPEG™) derivatives, (Product Catalog), pp. 1-51, (Updated: Jul. 18, 2005).

Quanta Biodesign, Ltd., Leading innovator, producer and provider of monodisperse discrete PEG™ (dPEG™) derivatives, (Product Catalog), pp. 1-51, (Updated: Nov. 17, 2005).

Renner, et al., "Allynadic-lmides" J. of Polymer Sci., Part A, 27:1301-1323, (1989).

Shaltout, et al., "Maleimide Functionalized Siloxane Resins", 576:15-20, (1999).

Shearwater Polymers, Inc., p. 2-49, (Catalog—Mar. 1995).

Shearwater Polymers, Inc., Polyethylene Glycol and Derivatives, pp. 1-53, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—2000).

Shearwater Corporation, Polyethylene Glycol and Derivatives for Biomedical Applications, pp. 1-17, (Catalog—2001).

Smyth, et al., "Reactions of N-Ethylmaleimide with Peptides and Amino Acids", Biochem. J., 91:589-595, (1964).

Office Communication dated Mar. 2, 2009, corresponding to European Application No. 06 788 037.7-2102.

Office Communication dated May 23, 2008, corresponding to European Application No. 06 788 037.7-2102.

International Search Report mailed Feb. 7, 2007, corresponding to PCT Application No. PCT/US2006/028271.

Written Opinion of the International Searching Authority, mailed Feb. 7, 2007, corresponding to PCT Application No. PCT/US2006/028271.

* cited by examiner

METHOD FOR PREPARING POLYMER MALEIMIDES

CROSS REFERENCE TO RELATED APPLICATION

This application claims the benefit of priority to U.S. provisional patent application Ser. No. 60/700,972, the contents of which are incorporated herein by reference in its entirety.

FIELD OF THE INVENTION

This invention relates to methods for preparing water soluble and non-peptidic polymers carrying maleimide functional groups, particularly maleimide-terminated poly(ethylene glycol) polymers, and to compositions and formulation containing the same.

BACKGROUND OF THE INVENTION

Maleimides are versatile derivatives that find extensive use in chemical synthesis and in biological and pharmacological applications. As Michael acceptors, maleimides react readily with sulfhydryl groups to form stable thioether bonds. This reaction is extensively used with proteins and the like where both sulfhydryl and amine groups are present. At approximately neutral pH, maleimides are highly selective, with sulfhydryl groups being about 1,000 times more reactive than amine groups (Smyth et al., Biochem. J., 91, 589, 1964; Gorin et al. Arch. Biochem. Biophys. 115, 593, 1966; Partis et al., J. Protein Chem, 2, 263-277, 1983). At higher pH values of 8 or above, the reaction of maleimides with amine groups begins to significantly compete (Brewer and Riehm, Anal. Biochem. 18, 248, 1967). While best known as Michael acceptors, maleimides are also useful for their reactivity as dienophiles (Baldwin et al., Tetrahedron Lett., 32, 5877, 1991; Philp and Robertson, J. Chem. Soc., Chem. Commun., 1998, 879; Bravo et al., Heterocycles, 53, 81, 2000) and as dipolarophiles (Grigg et al., J. Chem. Soc., Perkin Trans. 1, 1988, 2693; Konopikova et al., Collect. Czech. Chem. Commun., 57, 1521, 1991; Philp and Booth, Tetrahedron Lett., 39, 6987, 1998).

Maleimide groups can be used to facilitate covalent attachment of proteins and other molecules to polymers. For example, the hydrophilic polymer "poly(ethylene glycol)", abbreviated as "PEG", is often used to conjugate bioactive molecules and render them soluble in aqueous media (Harris et al. "Poly(Ethylene Glycol) Chemistry and Biological Applications", ACS Symposium Series, ACS, Washington, D.C., 1997). PEG-maleimide is an example of a reactive polymer suitable for reaction with thiol or amino groups on a biologically active molecule.

Many of the methods for preparing PEG maleimides involve connecting an activated PEG to a small linker molecule comprising a maleimide group, many of which are available commercially. There are a variety of shortcomings associated with several known PEG maleimides and methods for their production. For example, the so-called "linkerless" PEG maleimides, which have no linker group between the PEG and the maleimide group, are often prepared directly from a PEG amine using one of two methods. See U.S. Pat. No. 6,602,498. These methods, however, generally result in a relatively impure product inasmuch as a fairly significant amount of an open ring maleamic acid-containing derivative is present in the final product as will be discussed below.

In the first method disclosed in U.S. Pat. No. 6,602,498, a water soluble and non-peptidic polymer backbone is reacted with maleic anhydride to form an open ring amide carboxylic acid intermediate (a maleamic acid intermediate). The ring of the intermediate is then closed in a second step by heating the intermediate in the presence of acetic anhydride and a salt of acetic acid, such as sodium or potassium acetate, to a temperature of about 50° C. to about 140° C. for about 0.2 to about 5 hours. This two-step process is summarized in the Reaction Scheme I, provided below:

Reaction Scheme I

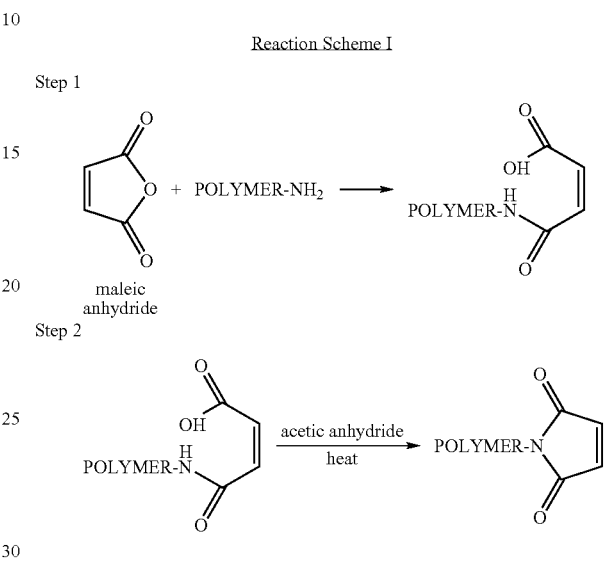

The crude maleimide-terminated, water-soluble polymer-containing composition made by this method may contain a substantial amount of the open ring maleamic acid intermediate. A major cause for the appearance of the open ring maleamic acid intermediate may lie with the heating step, especially if any acidic species is generated or is a contaminant in the acetic anhydride. Under these conditions, it is possible to isomerize the C=C bond and thus make ring closure difficult, if not impossible. As a result, it is desirable to purify the polymer product by some method, such as ion exchange chromatography, capable of removing the impurity. However, the maleimide ring system does not tolerate a chromatographic column bearing basic or nucleophilic sites, thus making purification more difficult. A second problem with this synthetic route stems from the use of PEG amine.

Similarly, Sakanoue et al., U.S. Patent Application Publication No. 2003/0065134 A1, describes a related method except that the PEG-maleimides produced therein comprise a propylene group rather than an ethylene group between the ultimate PEG oxygen and the maleimide nitrogen. The method described in Sakanoue et al., however, suffers from the same problems as mentioned above. Further, the reference teaches that the PEG amines are generally manufactured by reduction of a nitrile group using hydrogen and a nickel catalyst, which can lead to the introduction of additional impurities due to reaction between the amine product and an imine intermediate.

In a second synthetic route described in U.S. Pat. No. 6,602,498 (the "Aqueous N-alkoxycarbonylmaleimide route"), an N-alkoxycarbonylmaleimide is reacted with a polymeric amine to form a maleimide-terminated, water-soluble polymer product. A ring-opening and ring-closing reaction occurs similar to the one described above. The reaction is conducted over a slowly increasing temperature gradient in an aqueous sodium bicarbonate buffer at a pH of about 8.5. The maleimide group, however, is not stable at those conditions and undergoes hydrolysis to maleamic acid. Therefore, two parallel reactions occur during synthesis: formation of maleimide ring and maleimide ring hydrolysis.

One approach for addressing the problem would be to stop the reaction at a time when a maximum amount of the maleimide-terminated, water-soluble polymer product is formed. While this approach appears sound in theory, it is almost an impossible task in commercial practice due to the changing reaction temperature wherein it can be difficult to reproducibly achieve the temperature gradient during consecutive manufacturing batches. For example, consecutive commercial batches of certain maleimide-terminated, water-soluble polymers were found to have maleimide purity from 65 to 80%, and maleamic acid content of about 20 to 35%. Again, chromatography is not a viable option because of the sensitivity of the maleimide group to the functional groups of the ion exchange column. Furthermore, even if it were possible to reproducibly control the temperature gradient and stop the reaction at the proper time, the approach requires close monitoring and additional equipment (e.g., thermocouples, heat jackets, and so forth), thereby adding complexity to the approach.

Other approaches for preparing maleimide-terminated, water-soluble polymers are described in International Patent Publication WO 05/056636. In one approach (labeled as "Reaction Scheme II" below) a polymer comprising a leaving group ("LG") and a salt of an imide (shown as the potassium salt of a tricyclic amide) are reacted via nucleophilic substitution to form a polymer intermediate, which is then followed by a reverse Diels-Alder reaction to provide a maleimide functionalized polymer and furan.

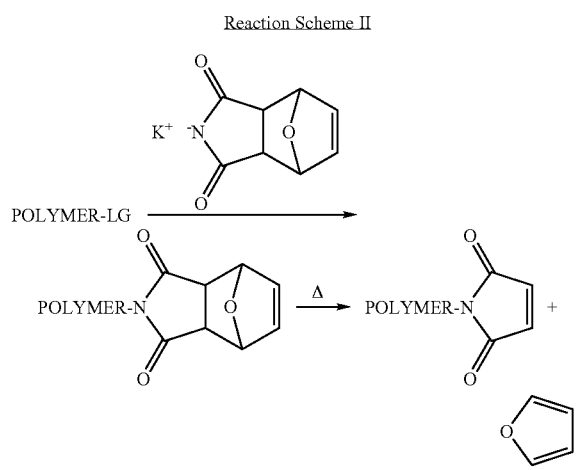

Reaction Scheme II

Although the reaction shown above utilizes relatively simple functionalized polymers and Diels-Alder adduct reagents that react to form so-called "linkerless" maleimides (meaning the maleimide group is directly attached to the polymer), the reaction requires not commercially available reagents.

Notwithstanding the approaches described above, there remains a need to provide still other approaches for preparing maleimide-terminated, water-soluble polymers so that, for example, the approach best suited for a particular need can be used. The novel approach described herein is believed to provide, among other things, maleimide-terminated polymers in high yield and free from significant amounts of polymeric impurities, particularly significant amounts of polymer impurities that cannot be readily removed using conventional purification techniques, such as ion exchange chromatography.

SUMMARY OF THE INVENTION

In one or more embodiments, a method for preparing a substituted maleamic acid-terminated, water-soluble polymer is provided, the method comprising:

a) combining an amine-terminated, water-soluble polymer with a maleimide reagent under substantially nonaqueous conditions to form a substituted maleamic acid-terminated, water-soluble polymer; and a') optionally, isolating the substituted maleamic acid-terminated, water-soluble polymer.

In one or more embodiments, a method for preparing a maleimide-terminated, water-soluble polymer is provided, the method comprising:

a) combining an amine-terminated, water-soluble polymer with a maleimide reagent under substantially nonaqueous conditions to form a substituted maleamic acid-terminated, water-soluble polymer; and b) exposing the maleamic acid-terminated, water-soluble polymer to elimination conditions under substantially nonaqueous conditions to thereby result in a maleimide-terminated, water-soluble polymer.

In one or more embodiments of the invention, a maleimide-terminated, water-soluble polymer-containing composition is provided, the composition resulting from the method comprising:

a) combining an amine-terminated, water-soluble polymer with a maleimide reagent under substantially nonaqueous conditions to form a maleamic acid-terminated, water-soluble polymer; and b) exposing the maleamic acid-terminated, water-soluble polymer to elimination conditions under substantially nonaqueous conditions to thereby result in a maleimide-terminated, water-soluble polymer-containing composition.

In one or more embodiments of the invention, a method for preparing a conjugate-containing composition is provided, the method comprising combining a thiol-containing biologically active agent with a maleimide-terminated, water-soluble polymer as provided herein to thereby result in a conjugate-containing composition.

In one or more embodiments of the invention, a conjugate-containing composition is provided, the composition resulting from the method comprising combining a thiol-containing active agent with a maleimide-terminated, water-soluble polymer-containing composition as provided herein.

In one or more embodiments of the invention, a compound is provided, the compound, in isolated form, has the following structure:

(Formula I)

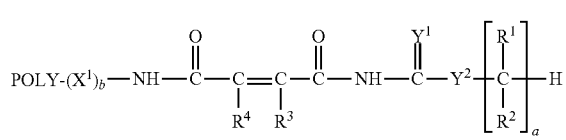

wherein:
POLY is a water-soluble polymer;
(b) is zero or one;
$X^1$, wherein present, is a spacer moiety;
$Y^1$ is O or S;
$Y^2$ is O or S;

(a) is an integer from 1 to 20;

$R^1$, in each instance, is independently H or an organic radical;

$R^2$, in each instance, is independently H or an organic radical;

$R^3$, in each instance, is independently H or an organic radical; and $R^4$, in each instance, is independently H or an organic radical.

DETAILED DESCRIPTION OF THE INVENTION

Before describing one or more embodiments of the present invention in detail, it is to be understood that this invention is not limited to the particular polymers, reagents, and the like, as such may vary.

It must be noted that, as used in this specification and the claims, the singular forms "a," "an," and "the" include plural referents unless the context clearly dictates otherwise. Thus, for example, reference to "a polymer" includes a single polymer as well as two or more of the same or different polymers, reference to "a drying agent" refers to a single drying agent as well as two or more of the same or different drying agents, and the like.

In describing and claiming the present invention(s), the following terminology will be used in accordance with the definitions provided below.

"PEG," "polyethylene glycol" and "poly(ethylene glycol)" as used herein, are interchangeable. Typically, PEGs for use in accordance with the invention comprise the following structure: "—$(OCH_2CH_2)_n$—" where (n) is 2 to 4000. As used herein, PEG also includes "—$CH_2CH_2$—O$(CH_2CH_2O)_n$ —$CH_2CH_2$—" and "—$(OCH_2CH_2)_nO$—," depending upon whether or not the terminal oxygens have been displaced. Throughout the specification and claims, it should be remembered that the term "PEG" includes structures having various terminal or "end capping" groups. The term "PEG" also means a polymer that contains a majority, that is to say, greater than 50%, of —$OCH_2CH_2$— or —$CH_2CH_2O$— repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or endpoint of a polymer having an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3(OCH_2CH_2)_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer as described herein, means a polymer that in its entirety is not found in nature. A non-naturally occurring polymer may, however, contain one or more monomers or segments of monomers that are naturally occurring, so long as the overall polymer structure is not found in nature.

The term "water soluble" as in a "water-soluble polymer" is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight in the context of a water-soluble polymer, such as PEG, can be expressed as either a number-average molecular weight or a weight-average molecular weight. Unless otherwise indicated, all references to molecular weight herein refer to the weight-average molecular weight. Both molecular weight determinations, number-average and weight-average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03. As used herein, references will at times be made to a single water-soluble polymer having either a weight-average molecular weight or number-average molecular weight; such references will be understood to mean that the single-water soluble polymer was obtained from a composition of water-soluble polymers having the stated molecular weight.

The terms "active" or "activated" when used in conjunction with a particular functional group, refer to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" or "linker" are used herein to refer to an atom or a collection of atoms used to link interconnecting moieties such as a terminus of a polymer and an active agent or an electrophile or nucleophile of an active agent. The spacer moiety may be hydrolytically stable or may include a physiologically hydrolyzable or enzymatically degradable linkage.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched. Non-limiting examples of lower alkyl include methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy; lower phenyl; substituted phenyl; and the like. "Substituted aryl" is aryl having one or more noninterfering substituents. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl, or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, aryl and substituted aryl.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucleophilic group" refers to an ion or atom or collection of atoms that may be ionic having a nucleophilic center, i.e., a center that is seeking an electrophilic center or capable of reacting with an electrophile.

A "physiologically cleavable" or "hydrolyzable" bond is a bond that reacts with water (i.e., is hydrolyzed) under physiological conditions. Preferred are bonds that have a hydrolysis half-life at pH 8, 25° C. of less than about 30 minutes. The tendency of a bond to hydrolyze in water will depend not only on the general type of linkage connecting two given atoms but also on the substituents attached to these two given atoms. Appropriate hydrolytically unstable or weak linkages include but are not limited to carboxylate ester, phosphate ester, anhydrides, acetals, ketals, acyloxyalkyl ether, imine, orthoester, peptide and oligonucleotide.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethane, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient" refers to an excipient that may optionally be included in a composition and that causes no significant adverse toxicological effects to a patient upon administration.

"Therapeutically effective amount" is used herein to mean the amount of a conjugate that is needed to provide a desired level of the conjugate (or corresponding unconjugated active agent) in the bloodstream or in the target tissue following administration. The precise amount will depend upon numerous factors, e.g., the particular active agent, the components and physical characteristics of the therapeutic composition, the intended patient population, the mode of delivery, individual patient considerations, and the like, and can readily be determined by one skilled in the art.

"Multi-functional" means a polymer having three or more functional groups contained therein, where the functional groups may be the same or different. Multi-functional polymeric reagents will typically contain a number of functional groups in one or more of the following ranges: from about 3-100 functional groups; from 3-50 functional groups; from 3-25 functional groups; from 3-15 functional groups; from 3 to 10 functional groups. Exemplary numbers of functional groups include 3, 4, 5, 6, 7, 8, 9 and 10 functional groups within the polymer backbone.

"Optional" or "optionally" means that the subsequently described circumstance may or may not occur, so that the description includes instances where the circumstance occurs and instances where it does not.

"Substantially" (unless specifically defined for a particular context elsewhere or the context clearly dictates otherwise) means nearly totally or completely, for instance, satisfying one or more of the following: greater than 50%, 51% or greater, 75% or greater, 80% or greater, 90% or greater, and 95% or greater of the condition.

The phrase "substantially nonaqueous conditions" means a composition or reaction medium having less than 10,000 parts per million of water (less than 1%), more preferably having less than 1,000 parts per million of water (less than 0.1%), still more preferably less than 100 parts per million of water (less than 0.01%), still more preferably less than 10 parts per million of water (less than 0.001%). Preferably, but not necessarily, substantially nonaqueous conditions includes an inert atmosphere.

Unless the context clearly dictates otherwise, when the term "about" precedes a numerical value, the numerical value is understood to mean±10% of the stated numerical value.

Method For Preparing A Substituted Maleamic Acid-Terminated, Water-Soluble Polymer In one or more embodiments of the present invention, a method for preparing a substituted maleamic acid-terminated, water-soluble polymer is provided. The method comprises:

a) combining an amine-terminated, water-soluble polymer with a maleimide reagent under substantially nonaqueous conditions to form a substituted maleamic acid-terminated, water-soluble polymer; and a') optionally, isolating the substituted maleamic acid-terminated, water-soluble polymer.

The combining step requires, as a starting material, an amine-terminated, water-soluble polymer. As used herein, an "amine-terminated, water-soluble polymer" is any water-soluble polymer that bears at least one amine group ("—NH$_2$"), regardless of whether the amine group is actually located at a terminus of the water-soluble polymer. Typically, although not necessarily, the amine-terminated, water-soluble polymer will have only one amine group, but the amine-terminated, water-soluble polymer can have more than one amine group. Thus, the amine-terminated, water-soluble polymer can (for example) have a total number of amine groups of any one of one, two, three, four, five, six, seven, eight, nine and ten.

An exemplary amine-terminated, water-soluble polymer comprises the following structure:

POLY-(X$^2$)$_c$—NH$_2$     (Formula II)

wherein:

POLY is a water-soluble polymer (preferably linear or branched, and preferably is CH$_3$O—(CH$_2$CH$_2$O)$_n$—CH$_2$CH$_2$—, wherein (n) is 2 to 4000 when POLY is linear);

(c) is zero or one (preferably zero); and

X$^2$, wherein present, is a spacer moiety.

The combining step also requires a maleimide reagent. The maleimide reagent is a reagent that—upon combination with an amine-terminated, water-soluble polymer—will result in the formation of one of the following: a maleimide-terminated, water-soluble polymer; or a substituted maleamic acid-terminated, water-soluble polymer.

An exemplary maleimide reagent comprises the following structure:

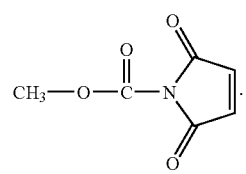
(Formula III)

wherein:

Y$^1$ is O or S (preferably O);

Y$^2$ is O or S (preferably O);

(a) is an integer from 1 to 20 (preferably one or two);

R$^1$, in each instance, is independently H or an organic radical (preferably H);

R$^2$, in each instance, is independently H or an organic radical (preferably H);

R$^3$, in each instance, is independently H or an organic radical (preferably H); and R$^4$, in each instance, is independently H or an organic radical (preferably H).

A preferred maleimide reagent is an N-alkoxycarbonylmaleimide, particularly where alkoxy is lower alkoxy. A preferred N-alkoxycarbonylmaleimide, N-methoxycarbonylmaleimide, is shown below:

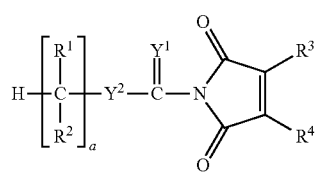
(Formula IV)

The combining step includes bringing the amine-terminated, water-soluble polymer in contact with the maleimide reagent and can be accomplished in any method known to those of ordinary skill in the art. For example, a composition comprising the amine-terminated, water-soluble polymer and a composition comprising the maleimide reagent can be combined in a reaction vessel. The combining step is, however, carried out to minimize the introduction of water.

Following the combining step, the method for preparing a substituted maleamic acid-terminated, water-soluble polymer, optionally includes the step of isolating the substituted maleamic acid-terminated, water-soluble polymer.

When it is intended to isolate the substituted maleamic acid-terminated, water-soluble polymer (and thus carry out the optional step of isolating the substituted maleamic acid-terminated, water-soluble polymer), any art-known technique can be used to isolate the substituted maleamic acid-terminated, water-soluble polymer and the invention is not limited in this regard. For example, isolation techniques selected from the group consisting of chromatography (e.g., silica-gel chromatography, HPLC chromatography, affinity-based chromatography, ion-exchange chromatography, and so forth), electrophoresis, precipitation (including, for example, recrystallization) and extraction can be used to isolate the substituted maleamic acid-terminated, water-soluble polymer. A preferred isolation technique is precipitation which can be accomplished using art-known methods (such as adding an excess of isopropyl alcohol, diethyl ether, MTBE, heptane, THF, hexane, and so forth, to cause the product to precipitate). Precipitation techniques will yield a dried substituted maleamic acid-terminated, water-soluble polymer. Other techniques can also be used to result in the dried substituted maleamic acid-terminated, water-soluble polymer.

The substituted maleamic acid-terminated, water-soluble polymer can take any number of forms. A preferred form is a substituted maleamic acid-terminated, water-soluble polymer comprising the following the following structure:

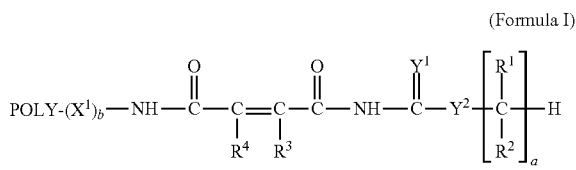

(Formula I)

wherein:
POLY is a water-soluble polymer;
(b) is zero or one;
X¹, wherein present, is a spacer moiety;
Y¹ is O or S;
Y² is O or S;
(a) is an integer from 1 to 20;
R¹, in each instance, is independently H or an organic radical;
R², in each instance, is independently H or an organic radical;
R³, in each instance, is independently H or an organic radical; and
R⁴, in each instance, is independently H or an organic radical.

It is preferred that a substituted maleamic acid-terminated, water-soluble polymer is provided in isolated form, meaning a composition wherein at least about 70% (more preferably at least 80%, and most preferably at least 90%) of all polymer species in the composition is in the substituted maleamic acid-terminated, water-soluble polymer form (and not in the amine-terminated, water-soluble form or the maleimide-terminated, water-soluble polymer form).

Before using any isolated substituted maleamic acid-terminated, water-soluble polymer, it is typical to carry out the additional step of redissolving the isolated (and typically dried) substituted maleamic acid-terminated, water-soluble polymer to regenerate the maleamic acid-terminated, water-soluble polymer in a nonaqueous liquid system.

The steps of the method used to prepare a maleimide-terminated, water-soluble polymer are typically carried out in an organic solvent. Although any organic solvent can be used and the invention is not limited in this regard, exemplary organic solvents include those solvents selected from the group consisting of halogenated aliphatic hydrocarbons, alcohols, aromatic hydrocarbons, alcohols, halogenated aromatic hydrocarbons, amides (including DMF), nitrites (including acetonitriles), ketones (including acetone), acetates (including ethyl acetate), ethers, cyclic ethers, and combinations thereof. Examples of preferred organic solvents include those selected from the group consisting of methylene chloride (or dichloromethane), chloroform, octanol, toluene, methyl t-butyl ether, THF (tetrahydrofuran), ethyl acetate, diethylcarbonate, acetone, acetonitrile, DMF (dimethyl formamide), DMSO, dimethylacetamide, N-cyclohexylpyrrolidinone, cyclohexane and combinations thereof.

The method for preparing a substituted maleamic acid-terminated, water-soluble polymer has utility as, among other things, providing an intermediate that is useful in the formation of a maleimide-terminated, water-soluble polymer (as will be discussed herein). By performing this method, it is possible to provide greater, reproducible yields of the substituted maleamic acid-terminated, water-soluble polymer from the amine-terminated, water-soluble polymer, thereby providing a more pure intermediate that can result in a more pure maleimide-terminated polymer composition and corresponding conjugate composition formed therefrom. Furthermore, the method provides for compositions that have less maleamic acid-based impurities in the composition.

Method For Preparing a Maleimide-Terminated, Water-Soluble Polymer

In one or more embodiments of the invention, a method for preparing a maleimide-terminated, water-soluble polymer is provided, the method comprising a) combining an amine-terminated, water-soluble polymer with a maleimide reagent under substantially nonaqueous conditions to form a substituted maleamic acid-terminated, water-soluble polymer; and b) exposing the maleamic acid-terminated, water-soluble polymer to elimination conditions under substantially nonaqueous conditions to thereby result in a maleimide-terminated, water-soluble polymer.

The step of combining an amine-terminated, water-soluble polymer with a maleimide reagent under substantially nonaqueous conditions to form a substituted maleamic acid-terminated, water-soluble polymer can be carried out as described above with respect to the method for preparing a substituted maleamic acid-terminated, water-soluble polymer.

Once the combining step has been carried out, the present method for preparing a maleimide-terminated, water-soluble polymer also includes the optional steps of isolating and redissolving the substituted maleamic acid-terminated, water-soluble polymer. Each of these optional steps (the optional isolating step and optional redissolving step) can be carried out as described above with respect to the method for preparing a substituted maleamic acid-terminated, water-soluble polymer.

The steps of the present method for preparing a maleimide-terminated, water-soluble polymer include the step of exposing the maleamic acid-terminated, water-soluble polymer to elimination conditions comprises heating the maleamic acid-terminated, water-soluble polymer. Any art-known elimination conditions can be used and the invention is not limited in this regard. For example, suitable elimination conditions comprise refluxing the acid-terminated, water-soluble polymer at a temperature of greater than at least about 35° C., more preferably at least about 40° C.

Exposure to elimination conditions can also include removing water from the reaction medium, by for example, exposing the maleamic acid-terminated, water-soluble polymer to a drying agent (such as adding $NaHCO_3$, $Na_2CO_3$, $CaCl_2$, $CaSO_4$, $MgSO_4$, KOH, $Na_2SO_4$, $K_2CO_3$, $KHCO_3$ and combinations thereof), a molecular sieve (e.g., aluminum silicates), azeotropic distillation and combinations of any of the foregoing.

Catalysts can also be used to enhance the kinetics of the method. In this regard it is preferred to carry out the present method for preparing a maleimide-terminated, water-soluble polymer in the presence of a catalyst such as a non-nucleophilic amine catalyst or a basic catalyst. With regard to non-nucleophilic amine catalysts, sterically hindered non-nucleophilic amine catalysts are preferred. Examples of non-nucleophilic amine catalysts include those selected from the group consisting of DMAP (N,N-dimethyl-4-aminopyridine), DBU (1,8-diazabicyclo[5.4.0]undec-7-ene), DABCO (1,4-diazabicyclo[2.2.2]octane), diisopropylethylamine, triethylamine, n-methyl morpholine. Examples of sterically hindered non-nucleophilic amine catalysts include DMAP (N,N-dimethyl-4-aminopyridine), DBU (1,8-diazabicyclo[5.4.0]undec-7-ene), DABCO (1,4-diazabicyclo[2.2.2]octane), and diisopropylethylamine. Examples of basic catalysts include sodium carbonate, sodium bicarbonate, potassium carbonate and potassium bicarbonate.

The steps of the method used to prepare a maleimide-terminated, water-soluble polymer are typically carried out in an organic solvent. Although any organic solvent can be used and the invention is not limited in this regard, exemplary organic solvents include those solvents selected from the group consisting of halogenated aliphatic hydrocarbons, alcohols, aromatic hydrocarbons, alcohols, halogenated aromatic hydrocarbons, amides (including DMF), nitrites (including acetonitriles), ketones (including acetone), acetates (including ethyl acetate), ethers, cyclic ethers, and combinations thereof. Examples of preferred organic solvents include those selected from the group consisting of methylene chloride (or dichloromethane), chloroform, octanol, toluene, methyl t-butyl ether, THF, ethyl acetate, diethylcarbonate, acetone, acetonitrile, DMF, DMSO, dimethylacetamide, N-cyclohexylpyrrolidinone, cyclohexane and combinations thereof.

The maleimide-terminated, water-soluble polymer can have a variety of structures and will depend upon the structure of the substituted maleamic acid-terminated, water-soluble polymer from which it derives. An exemplary, maleimide-terminated, water-soluble polymer prepared in accordance with the presence method will be of the following structure:

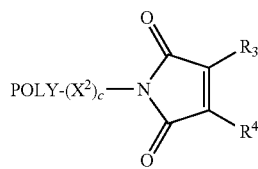

(Formula V)

wherein each of POLY, $X^2$ and (c) are defined as provided in Formula II and each of $R^3$ and $R^4$ are defined as provided in Formula III.

A particularly preferred maleimide-terminated, water-soluble polymer will comprise the following structure:

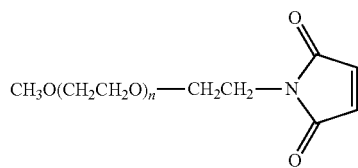

(Formula VI)

wherein (n) is an integer from 2 to about 4000.

Maleimide-Terminated, Water-Soluble Polymer-Containing Composition

In one or more embodiments of the invention, a maleimide-terminated, water-soluble polymer-containing composition is provided, the composition resulting from the method comprising:

a) combining an amine-terminated, water-soluble polymer with a maleimide reagent under substantially nonaqueous conditions to form a maleamic acid-terminated, water-soluble polymer; and b) exposing the maleamic acid-terminated, water-soluble polymer to elimination conditions under substantially non-aqueous conditions to thereby result in a maleimide-terminated, water-soluble polymer-containing composition.

Thus, included within the invention are compositions of maleimide-terminated, water-soluble polymers formed in accordance with the method provided. The compositions resulting from the method are believed to have greater purity than previously known methods. Specifically, the maleimide-terminated, water-soluble polymer-containing compositions possess relatively low percentages of maleamic acid terminated, water-soluble polymers (e.g., typically less than four percent and often less than two percent). In addition, the maleimide-terminated, water-soluble polymer-containing compositions are substantially free of furan, preferably completely free of furan.

In another embodiment of the invention, maleimide-terminated, water-soluble polymer-containing compositions are provided, such compositions comprising polymeric species wherein at least 70% of the polymeric species in the composition are maleimide-terminated, water-soluble polymers and further wherein the composition comprises open ring ester polymeric species. The open ring ester polymeric species has the structure

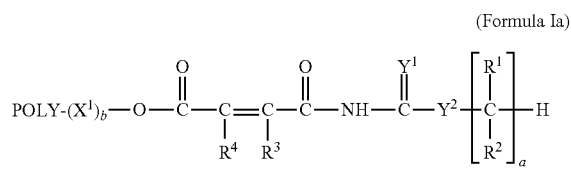

(Formula Ia)

wherein each of POLY, $X^1$, (a), (b), $R^1$, $R^2$, $R^3$, $R^4$, $Y^1$ and $Y^2$ is as defined with respect to Formula I. This "open ring ester" is not found in connection with the aqueous-based N-alkoxy-carbonylmaleimide route for preparing maleimide-terminated, water-soluble polymers.

Method for Preparing a Conjugate-Containing Composition

In one or more embodiments of the invention, a method for preparing a conjugate-containing composition is provided, the method comprising combining (in a reaction vessel) a thiol-containing biologically active agent (such as a cysteine-containing protein or polypeptide) with a maleimide-terminated, water-soluble polymer composition as provided herein to thereby result in a conjugate-containing composition. Although approaches for conjugating maleimide-terminated, water-soluble polymers to thiol-containing biologically active agents have been described, an exemplary approach involves dissolving the maleimide-terminated, water-soluble polymer in deionized water to make a 10% reagent solution and combining with a thiol-containing biologically active agent (at a five- to twenty-fold molar excess the polymer to the thiol-containing biologically active agent) and mixing well. After about one hour of reaction at room temperature, the reaction vial can cooled and mixed for about twelve hours to ensure sufficient reaction time. The pH of the reaction can be conducted at about 7.

Thus, included within the invention are methods for preparing conjugate-containing compositions using the inventive maleimide-terminated, water-soluble polymer compositions of the invention. The thiol-containing active agent can be any protein bearing a cysteine residue that is not involved in intraprotein disulfide binding.

Conjugate-Containing Compositions

In one or more embodiments of the invention, a conjugate-containing composition is provided, the composition resulting from the method comprising combining a thiol-containing active agent with a maleimide-terminated, water-soluble polymer-containing composition as provided herein.

Thus, included within the invention are conjugate-containing compositions formed in accordance with the provided method for preparing conjugate-containing compositions. The compositions resulting from the method are believed to have greater purity than previously known methods. The conjugate-containing compositions, like the maleimide-terminated, water soluble polymer compositions used to create them, possess relatively low percentages of maleamic acid terminated, water-soluble polymers (e.g., typically less than four percent and often less than two percent). In addition, the conjugate-containing compositions are substantially free of furan, preferably completely free of furan.

The Water-Soluble Polymer ("POLY")

As used herein, the term "water-soluble polymer" includes those water soluble polymers that are biocompatible and non-immunogenic and specifically excludes any water soluble polymer segments that are not biocompatible and nonimmunogenic. With respect to biocompatibility, a substance is considered biocompatible if the beneficial effects associated with use of the substance alone or with another substance (e.g., active agent) in connection with living tissues (e.g., administration to a patient) outweighs any deleterious effects as evaluated by a clinician, e.g., a physician. With respect to nonimmunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water soluble polymer segments described herein as well as conjugates are biocompatible and nonimmunogenic.

When referring to the polymer, it is to be understood that the polymer can be any of a number of water soluble and non-peptidic polymers, such as those described herein as suitable for use in the present invention. Preferably, poly (ethylene glycol) (i.e., PEG) is the polymer. The term PEG includes poly(ethylene glycol) in any of a number of geometries or forms, including linear forms, branched or multi-arm forms (e.g., forked PEG or PEG attached to a polyol core), pendant PEG, or PEG with degradable linkages therein, to be more fully described below.

The number of functional groups carried by the polymer and the position of the functional groups may vary. Typically, the polymer will comprise 1 to about 25 functional groups, preferably 1, 2, 3, 4, 5, 6, 7, 8, 9, or 10 functional groups. Linear polymers, such as PEG polymers, will typically comprise one or two functional groups positioned at the terminus of the polymer chain. If the PEG polymer is monofunctional (i.e., linear mPEG), the polymer will include a single functional group. If the PEG polymer is difunctional, the polymer may contain two independently selected functional groups, one at each terminus of the polymer chain. As would be understood, multi-arm or branched polymers may comprise a greater number of functional groups.

Multi-armed or branched PEG molecules, such as those described in U.S. Pat. No. 5,932,462, which is incorporated by reference herein in its entirety, can also be used as the PEG polymer. Generally speaking, a multi-armed or branched polymer possesses two or more polymer "arms" extending from a central branch point. For example, an exemplary branched PEG polymer has the structure:

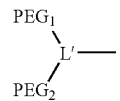

wherein $PEG_1$ and $PEG_2$ are PEG polymers in any of the forms or geometries described herein, and which can be the same or different, and L' is a hydrolytically stable linkage. An exemplary branched PEG has the structure:

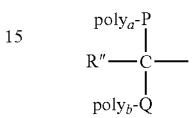

wherein $poly_a$ and $poly_b$ are PEG backbones, such as methoxy poly(ethylene glycol); R" is a nonreactive moiety, such as H, methyl or a PEG backbone; and P and Q are nonreactive linkages. In a preferred embodiment, the branched PEG polymer is methoxy poly(ethylene glycol) disubstituted lysine.

The branched PEG structure can be attached to a third oligomer or polymer chain as shown below:

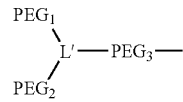

wherein $PEG_3$ is a third PEG oligomer or polymer chain, which can be the same or different from $PEG_1$ and $PEG_2$.

The PEG polymer can alternatively comprise a forked PEG. Generally speaking, a polymer having a forked structure is characterized as having a polymer chain attached to two or more functional groups via covalent linkages extending from a hydrolytically stable branch point in the polymer. An example of a forked PEG is represented by $PEG-YCHZ_2$, where Y is a linking group and Z is an activated terminal group for covalent attachment to a biologically active agent. The Z group is linked to CH by a chain of atoms of defined length. U.S. Pat. No. 6,362,254, the contents of which are incorporated by reference herein, discloses various forked PEG structures capable of use in the present invention. The chain of atoms linking the Z functional groups (e.g., hydroxyl groups) to the branching carbon atom serve as a tethering group and may comprise, for example, an alkyl chain, ether linkage, ester linkage, amide linkage, or combinations thereof.

The PEG polymer may comprise a pendant PEG molecule having reactive groups (e.g., hydroxyl groups) covalently attached along the length of the PEG backbone rather than at the end of the PEG chain. The pendant reactive groups can be attached to the PEG backbone directly or through a linking moiety, such as an alkylene group.

In addition to the above-described forms of PEG, the polymer can also be prepared with one or more hydrolytically stable or degradable linkages in the polymer backbone, including any of the above described polymers. For example, PEG can be prepared with ester linkages in the polymer backbone that are subject to hydrolysis. As shown below, this hydrolysis results in cleavage of the polymer into fragments of lower molecular weight:

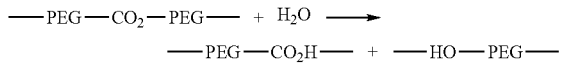

Other hydrolytically degradable linkages, useful as a degradable linkage within a polymer backbone, include carbonate linkages; imine linkages resulting, for example, from reaction of an amine and an aldehyde (see, e.g., Ouchi et al., Polymer Preprints, 38(1):582-3 (1997), which is incorporated herein by reference.); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between acid derivatives and an alcohol; and oligonucleotide linkages formed by, for example, a phosphoramidite group, e.g., at the end of a polymer, and a 5' hydroxyl group of an oligonucleotide. The use of many of the above-described degradable linkages is less preferred due to nucleophilic reactivity of many of the unstable linkages with amine groups.

It is understood by those skilled in the art that the term poly(ethylene glycol) or PEG represents or includes all the above forms of PEG.

Any of a variety of other polymers comprising other non-peptidic and water soluble polymer chains can also be used in the present invention. The polymer can be linear, or can be in any of the above-described forms (e.g., branched, forked, and the like). Examples of suitable polymers include, but are not limited to, other poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxyacetic acid), poly(acrylic acid), poly(vinyl alcohol), polyphosphazene, polyoxazolines, poly(N-acryloylmorpholine), such as described in U.S. Pat. No. 5,629,384, which is incorporated by reference herein in its entirety, and copolymers, terpolymers, and mixtures thereof.

Although the molecular weight of the water soluble polymer can vary depending on the desired application, the configuration of the polymer structure, the degree of branching, and the like, the molecular weight will satisfy one or more of the following values: greater than 100 Daltons; greater than 200 Daltons; greater than 400 Daltons; greater than 500 Daltons, greater than 750 Daltons; greater than 900 Daltons; greater than 1,000 Daltons, greater than 1,400 Daltons; greater than 1,500 Daltons, greater than 1,900 Daltons; greater than 2,000 Daltons, greater than 2,200 Daltons; greater than 2,500 Daltons, greater than 3,000 Daltons; greater than 4,000 Daltons, greater than 4,900 Daltons; greater than 5,000 Daltons, greater than 6,000 Daltons; greater than 7,000 Daltons, greater than 7,500 Daltons; greater than 9,000 Daltons; greater than 10,000 Daltons; greater than 11,000 Daltons; greater than 14,000 Daltons; greater than 15,000 Daltons; greater than 16,000 Daltons; greater than 19,000 Daltons; greater than 20,000 Daltons; greater than 21,000 Daltons; greater than 22,000 Daltons; greater than 25,000 Daltons; and greater than 30,000 Daltons. It is understood that the maximum limit of molecular weight for any given water soluble polymer segment useful herein is less than about 300,000 Daltons.

The molecular weight of the polymer will typically fall into at least one of the following ranges: from about 100 Daltons to about 100,000 Daltons; from about 200 Daltons to about 60,000 Daltons; from about 300 Daltons to about 40,000 Daltons.

Exemplary molecular weights for the water soluble polymer include about 100 Daltons, about 200 Daltons, about 300 Daltons, about 350 Daltons, about 400 Daltons, about 500 Daltons, about 550 Daltons, about 600 Daltons, about 700 Daltons, about 750 Daltons, about 800 Daltons, about 900 Daltons, about 1,000 Daltons, about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 50,000 Daltons, about 60,000 Daltons, and about 75,000 Daltons.

With respect to branched versions of the polymer, exemplary ranges of suitable sizes for the total molecular weight of the polymer (as based essentially on the combined weights of the two water soluble polymer portions) include the following: from about 200 Daltons to about 100,000 Daltons; from about 1,000 Daltons to about 80,000 Daltons; from about 2,000 Daltons to about 50,000 Daltons; from about 4,000 Daltons to about 25,000 Daltons; and from about 10,000 Daltons to about 40,000 Daltons. More particularly, total weight average molecular weight of a branched version of the polymer of the invention corresponds to one of the following: 400; 1,000; 1,500; 2,000; 3000; 4,000; 10,000; 15,000; 20,000; 30,000; 40,000; 50,000; 60,000; or 80,000.

With respect to PEG, wherein a structure comprising a repeating ethylene oxide monomer, such as "—(CH$_2$CH$_2$O)$_n$—" or "—(OCH$_2$CH$_2$)$_n$," can be provided, preferred values for (n) include: from about 3 to about 3,000; from about 10 to about 3,000; from about 15 to about 3,000; from about 20 to about 3,000; from about 25 to about 3,000; from about 30 to about 3,000; from about 40 to about 3,000; from about 50 to about 3,000; from about 55 to about 3,000; from about 75 to about 3,000; from about 100 to about 3,000; and from about 225 to about 3,000.

The Spacer Moiety ("X$^1$", "X$^2$", and so forth)

Optionally, a spacer moiety can link the water-soluble polymer to the maleimide and/or from the maleimidyl moiety to the residue of a thiol-containing active agent. Exemplary spacer moieties include the following: —O—, —S—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—, —C(O)—O—

—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, —NH—C(O)—NH—(CH$_2$)$_{1-6}$—NH—C(O)—, —O—C(O)—CH$_2$—, —O—C(O)—CH$_2$—CH$_2$—, —O—C(O)—CH$_2$—CH$_2$—CH$_2$—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —CH$_2$—CH$_2$—CH$_2$—C(O)—NH—CH$_2$—CH$_2$—NH—C(O)—CH$_2$—CH$_2$—, O—C(O)—NH—[CH$_2$]$_f$—(OCH$_2$CH$_2$)$_n$—, and combinations of two or more of any of the foregoing, wherein (f) is 0 to 6, (n) is 0 to 20 (preferably 0 to 10, e.g., 0, 1, 2, 3, 4, 5, 6, 7, 8, 9 or 10, and more preferably 4). In addition, each of the foregoing carbon-containing spacer moieties can have a branched alkyl group attached thereto. Nonlimiting examples of bivalent cycloalkyl (e.g., cycloalkylene) groups include C$_{3-8}$ cycloalkyl, such as various isomers of cyclopropadiyl (e.g., 1,1-, cis-11,2-, or trans-1,2-cyclopropylene), cyclobutadiyl, cyclopentadiyl, cyclohexadiyl, and cycloheptadiyl. The cycloalkylene group can be substituted with one or more alkyl groups, preferably C$_1$-C$_6$ alkyl groups.

Biologically Active Conjugates

The present invention also includes stabilized biologically active conjugates comprising a nucleophilic biologically active molecule capable of Michael addition covalently attached to the reactive polymer through a succinimide ring linkage. The biologically active agent is preferably a protein bearing a thiol or amino group.

Suitable biologically active agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

Examples of active agents suitable for use in covalent attachment to the reactive polymer of the invention include, but are not limited to, calcitonin, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX insulin, pro-insulin, insulin analogues (e.g., monoacylated insulin as described in U.S. Pat. No. 5,922,675), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining stability and other parameters of the composition, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The invention also provides a method for administering a conjugate as provided herein to a patient suffering from a condition that is responsive to treatment with a conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the patient as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains. Although specific terms are employed herein, they are used in a generic and descriptive sense only and not for purposes of limitation.

All articles, books, patents and other publications referenced herein are hereby incorporated by reference in their entireties.

EXPERIMENTAL

The practice of the invention will employ, unless otherwise indicated, conventional techniques of organic synthesis, biochemistry, protein purification and the like, which are within the skill of the art. Such techniques are fully explained in the literature. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be accounted for. Unless indicated otherwise, temperature is in degrees C and pressure is at or near atmospheric pressure at sea level. Each of the following examples is considered to be instructive to one of ordinary skill in the art for carrying out one or more of the embodiments described herein. All $^1$H NMR data was generated by a 300 or 400 MHz NMR spectrometer manufactured by Bruker. In Examples 5 through 12, commercial grade mPEG(20 k Da)-amine was used having the following characterization: percent substitution of amine, 94.6 to 100%; percent hydroxy mPEG impurity, 0 to 4.2%; percent dimer (species formed from the reaction of two functionalized PEG species to each other), 0.6 to 2.1%; percent trimer (species formed from the reaction of three functionalized PEG species to each other), 0 to 0.3%.

Example 1

Preparation of a Substituted Maleamic Acid-Terminated, Water-Soluble Polymer

To a solution of mPEG (20 k Da)-amine (Nektar Therapeutics, 50.0 g, 0.0025 mol) in anhydrous dichloromethane (350 ml), N-methoxycarbonylmaleimide (0.80 g, 0.0051 mol) was added and the solution was stirred for one hour at room temperature under argon atmosphere. N,N-diisopropylethylamine (1.0 ml) was added and the mixture was stirred overnight at room temperature under argon atmosphere. Next the reaction mixture was concentrated by distilling off ~200 ml dischloromethane and the product was precipitated with ethyl ether. Yield after drying 46.3 g. NMR (d$_6$-DMSO): 3.24 ppm (s, PEG-OCH$_3$), 3.51 ppm (s, PEG backbone), 3.86 ppm (s, CH$_3$O—NH—), 6.20 ppm (m, —CH=CH—), 8.46 ppm (—NH).

Example 2

Preparation of mPEG (20 k Da)Maleimide

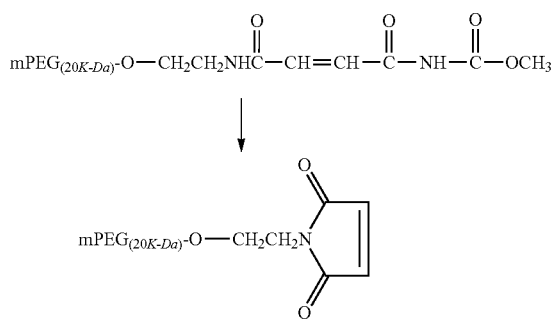

To the solution of the substituted maleamic acid-terminated, water-soluble polymer prepared in Example 1 (10.0 g), in anhydrous acetonitrile (100 ml) N,N-diisopropylethylamine (10 ml) was added and the reaction mixture was stirred for forty-four hours at room temperature under argon atmosphere. Next, the mixture was concentrated by distilling off ~80 ml acetonitrile and the product was precipitated with ethyl ether giving 8.5 g of mPEG$_{(20K\ Da)}$maleimide. NMR (d$_6$-DMSO): 3.24 ppm (s, PEG-OCH$_3$), 3.51 ppm (s, PEG backbone), 7.01 ppm (s, —CH=CH—, maleimide); substitution 93.5%.

Example 3

A Protocol for Preparing Substituted Maleamic Acid-Terminated, Water-Soluble Polymer

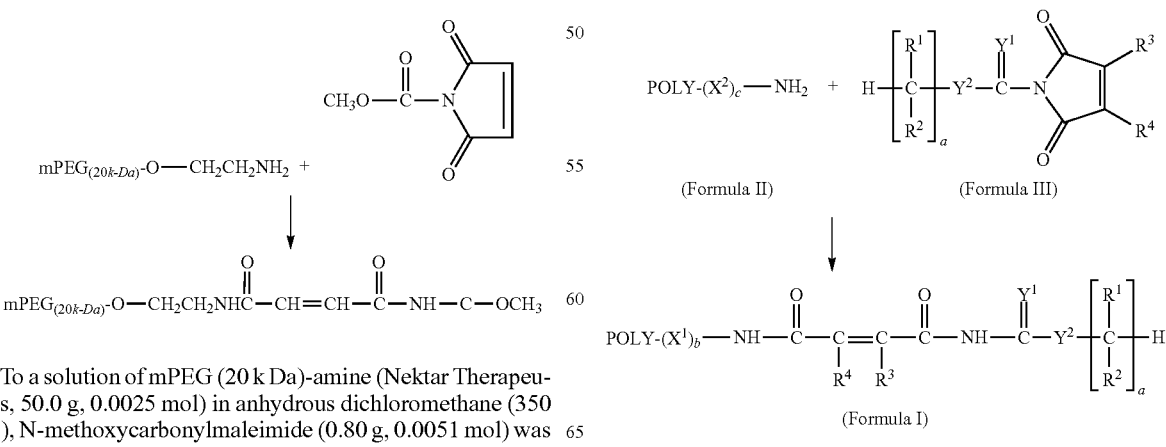

wherein (with respect to Formula II):

POLY is a water-soluble polymer (preferably linear or branched, and preferably is $CH_3O-(CH_2CH_2O)_n-CH_2CH_2-$, wherein (n) is 2 to 4000 when POLY is linear);

(c) is zero or one (preferably zero); and $X^2$, wherein present, is a spacer moiety, wherein (with respect to Formula III):

$Y^1$ is O or S;

$Y^2$ is O or S;

(a) is an integer from 1 to 20;

$R^1$, in each instance, is independently H or an organic radical;

$R^2$, in each instance, is independently H or an organic radical;

$R^3$, in each instance, is independently H or an organic radical; and $R^4$, in each instance, is independently H or an organic radical, wherein (with respect to Formula I):

POLY is a water-soluble polymer;

(b) is zero or one;

$X^1$, wherein present, is a spacer moiety;

$Y^1$ is O or S;

$Y^2$ is O or S;

(a) is an integer from 1 to 20;

$R^1$, in each instance, is independently H or an organic radical;

$R^2$, in each instance, is independently H or an organic radical;

$R^3$, in each instance, is independently H or an organic radical; and $R^4$, in each instance, is independently H or an organic radical.

Dissolve the amine-terminated, water-soluble polymer (Formula II) into dichloromethane (20% wt/v solution) and distill under reduced pressure at 40° C. until all the dichloromethane is removed. This will form an azeotropic mixture with water and effectively remove the water from the remaining polymer. Repeat this step once more. Place under vacuum to dry completely to a solid if desired (not necessary).

Redissolve the polymer in anhydrous dichloromethane (20% wt/v solution) under an inert gas atmosphere. Add 1.5 equivalents of a maleimide reagent (Formula III). Once dissolved, add 0.5 equivalents of diisopropylethylamine dropwise. Let stir at room temperature under inert atmosphere for at least one hour (overnight is fine, but may form closed-ring maleimide).

Distill off solvent under reduced pressure at 25-30° C. until a thick oil-like solution results (approximately 0.5-1.5 mL of solution per gram of water-soluble polymer, depending upon molecular weight). Add isopropyl alcohol slowly to the stirring solution (approximately 25 mL/g of water-soluble polymer). Let stir at room temperature for at least thirty minutes. Filter off the liquid. Add back enough isopropyl alcohol to make a slurry of the water-soluble polymer, and then filter off the liquid once again. Dry the solids under vacuum until all isopropyl alcohol is removed.

Example 4

A Protocol For Preparing a Maleimide-Terminated, Water-Soluble Polymer

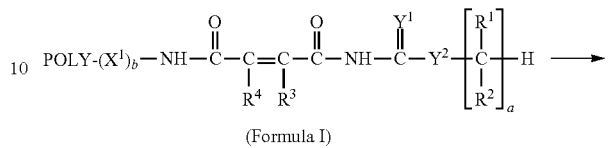

(Formula I)

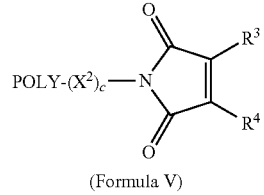

(Formula V)

wherein (with respect to Formula I):

POLY is a water-soluble polymer;

(b) is zero or one;

$X^1$, wherein present, is a spacer moiety;

$Y^1$ is O or S;

$Y^2$ is O or S;

(a) is an integer from 1 to 20;

$R^1$, in each instance, is independently H or an organic radical;

$R^2$, in each instance, is independently H or an organic radical;

$R^3$, in each instance, is independently H or an organic radical; and $R^4$, in each instance, is independently H or an organic radical, wherein (with respect to Formula V) each of POLY, $X^2$ and (c) are defined as provided in Formula II and each of $R^3$ and $R^4$ are defined as provided in Formula III.

Dissolve the substituted maleamic acid-terminated, water-soluble polymer from Example 3 into anhydrous dichloromethane to make a 10% wt/v solution. Add anhydrous sodium sulfate (0.5 g/g of PEG). Add anhydrous sodium carbonate (0.5 g/g of water-soluble polymer). Heat to reflux under inert gas atmosphere (approximately 40° C.). Stir at reflux for five hours. Remove heat and let cool to less than 35° C. Filter off solids. Distill off solvent under reduced pressure at 25-40° C. until a thick oil-like solution results. Precipitate with isopropyl alcohol as in Example 3.

Example 5

Nonaqueous Preparation of a Maleimide-Terminated, Water-Soluble Polymer

Azeotroped mPEG(20 k Da)-amine, 0.01 wt % butylated hydroxytoluene (BHT), and dichloromethane were combined at 40° C. Evaporation of the more volatile components was conducted using a rotary evaporator. The water content was tested and found to be 56 ppm (below 100 ppm is desired). To this mixture was added 0.5 g/g each of milled sodium carbonate and granular sodium sulfate. Following addition of the milled sodium carbonate and granular sodium sulfate, the mixture was stirred and cooled to 5° C. to form a cold PEG solution.

Separately, 3 eq (0.56 g) of N-methoxycarbonylmaleimide was dissolved in dichloromethane to make a 3% (w/v) solution. The resulting mixture was vortexed for 30 seconds. The vortexed mixture had a cloudy appearance. The vortexed mixture was added to the cold PEG solution and stirred for 21 hours at or about 5° C.

Following stirring, the mixture was heated gradually to about 40° C. and refluxed for over 45 minutes. Thereafter, samples were withdrawn to determine reaction completion by H NMR After 8.5 hours at reflux, the mixture was cooled to room temperature, filtered through a celite bed, and followed by removal of the dichloromethane solvent using a rotary evaporator and a bath at 30° C., thereby producing the an oil. The product was recovered by precipitation with isopropyl alcohol (IPA) (stirring for 30 minutes).

Analyses associated with this example are provided in Tables 1 and 2 and discussed in Example 13.

Example 6

Nonaqueous Preparation of a Maleimide-Terminated, Water-Soluble Polymer

The procedure of Example 5 was repeated, with the following exceptions/notations. Following addition of the milled sodium carbonate and granular sodium sulfate, the mixture was cooled to 5° C. for 10 hours. Reflux was conducted for 7 hours (which showed 6% precursor at the $6^{th}$ hour).

Analyses associated with this example are provided in Tables 1 and 2 and discussed in Example 13.

Example 7

Nonaqueous Preparation of a Maleimide-Terminated, Water-Soluble Polymer

The procedure of Example 5 was repeated, with the following exceptions/notations. Following addition of the milled sodium carbonate and granular sodium sulfate, the mixture was stirred and cooled to 5.7° C. for 9.5 hours. Rather than heating and then refluxing, the mixture was stirred at room temperature for 45 minutes prior to refluxing. Reflux was conducted for 6.5 hours (which showed 6% precursor at the 5th hour).

Analyses associated with this example are provided in Tables 1 and 2 and discussed in Example 13.

Example 8

Nonaqueous Preparation of a Maleimide-Terminated, Water-Soluble Polymer

The procedure of Example 5 was repeated, with the following exceptions/notations. Following addition of the milled sodium carbonate and granular sodium sulfate, the mixture was stirred and cooled to 5.75° C. initially and gradually cooled over 2 hours to 5° C. with stirring for 15 hours total. Rather than heating and then refluxing, the mixture was stirred at room temperature for 1 hour prior to refluxing. Reflux was conducted for 8 hours (which showed 12% precursor at the $6^{th}$ hour).

Analyses associated with this example are provided in Tables 1 and 2 and discussed in Example 13.

Example 9

Comparative Example

"Aqueous N-Alkoxycarbonylmaleimide Route"

A 17.5% solution (w/v) of mPEG amine (20 k Da) in 7.6% (w/v) sodium bicarbonate solution was cooled to 6° C. A 10% solution (w/v) of N-methoxycarbonylmaleimide (3 eq., 5.3%) in acetonitrile was added and the mixture and stirred for 15 minutes. Enough distilled water was added to the solution to double the volume. The solution was first cooled and then allowed to warm to 13° C. over 45 minutes.

The pH of the solution was adjusted to 3.0 with phosphoric acid and then enough sodium chloride was added to provide a salt solution of 15% sodium chloride (w/v). The salt solution was stirred for 15 minutes and then extracted with an equivalent volume of dichloromethane, thereby providing a dichloromethane solution.

The dichloromethane solution was dried with sodium sulfate (3.5 g/100 mL) and evaporated to result in an oil. Precipitation with isopropyl alcohol (17.5 mL/g), filtration and drying gave a white solid.

Analyses associated with this example are provided in Tables 1 and 2 and discussed in Example 13.

Example 10

Comparative Example

"Aqueous N-Alkoxycarbonylmaleimide Route"

A 17.5% solution (w/v) of mPEG amine (20 k Da) in 7.6% (w/v) sodium bicarbonate solution was cooled to 3.8 to 5.9° C. An excursion in temperature to room temperature overnight occurred due to chiller problems. A 10% solution (w/v) of N-methoxycarbonylmaleimide (3 eq., 4.4%) in acetonitrile was added and the mixture and stirred for 15 minutes. Enough distilled water was added to the solution to double the volume. The solution was first cooled and then allowed to warm to 13° C. over 45 minutes.

The pH of the solution was adjusted to 3.0 with phosphoric acid and then enough sodium chloride was added to provide a salt solution of 15% sodium chloride (w/v). The salt solution was stirred for 15 minutes and then extracted with an equivalent volume of dichloromethane, thereby providing a dichloromethane solution.

The dichloromethane solution was dried with sodium sulfate (3.5 g/100 mL) and evaporated to result in an oil. Precipitation with isopropyl alcohol (17.5 mL/g), filtration and drying gave a white solid.

Analyses associated with this example are provided in Tables 1 and 2 and discussed in Example 13.

Example 11

Comparative Example

"Aqueous N-Alkoxycarbonylmaleimide Route"

A 17.5% solution (w/v) of MPEG amine (20 k Da) in 7.6% (w/v) sodium bicarbonate solution was cooled to 4° C. A 10% solution (w/v) of N-methoxycarbonylmaleimide (3 eq., 5.4%) in acetonitrile was added and the mixture and stirred for 15 minutes. Enough distilled water was added to the solution to double the volume. The solution was first cooled and then allowed to warm to 8 to 9° C. over 45 minutes.

The pH of the solution was adjusted to 3.0 with phosphoric acid and then enough sodium chloride was added to provide a salt solution of 15% sodium chloride (w/v). The salt solution was stirred for 15 minutes and then extracted with an equivalent volume of dichloromethane, thereby providing a dichloromethane solution.

The dichloromethane solution was dried with sodium sulfate (3.5 g/100 mL) and evaporated to result in an oil. Precipitation with isopropyl alcohol (17.5 mL/g), filtration and drying gave a white solid.

Analyses associated with this example are provided in Tables 1 and 2 and discussed in Example 13.

Example 12

Comparative Example

"Aqueous N-Alkoxycarbonylmaleimide Route"

A 17.5% solution (w/v) of MPEG amine (20 k Da) in 7.6% (w/v) sodium bicarbonate solution was cooled to 6° C. A 10% solution (w/v) of N-methoxycarbonylmaleimide (3 eq., 5.3%) in acetonitrile was added and the mixture and stirred for 15 minutes. Enough distilled water was added to the solution to double the volume. The solution was first cooled and then allowed to warm to 13° C. over 45 minutes.

The pH of the solution was adjusted to 3.0 with phosphoric acid and then enough sodium chloride was added to provide a salt solution of 15% sodium chloride (w/v). The salt solution was stirred for 15 minutes and then extracted with an equivalent volume of dichloromethane, thereby providing a dichloromethane solution.

The dichloromethane solution was dried with sodium sulfate (3.5 g/100 mL) and evaporated to result in an oil. Precipitation with isopropyl alcohol (17.5 mL/g), filtration and drying gave a white solid.

Analyses associated with this example are provided in Tables 1 and 2 and discussed in Example 13.

Example 13

The products obtained from Examples 5 to 12 were analyzed using HPLC, GFC and $^1$H NMR. High Performance Liquid Chromatography (HPLC) was performed using an Agilent 1100 HPLC system (Agilent) using a Shodex Protein KW-803 GFC column with a mobile phase of 10 mM HEPES, flow rate of 1.0 mL/minute and temperature of 25° C. with use of an RI detector (product derivatized with a carboxylic acid functionalized thiol species, and substitution is determined by comparison of derivatized and underivatized spectra). GFC was performed using a Shodex Protein KW-803 GFC column with a mobile phase of 1× phosphate-buffered saline, flow rate of 1.0 mL/minute and temperature of 25° C. with use of an RI detector. The results are provided in Tables 1 and 2. With regard to Table 1, "% of Dimaleimidyl species" refers to a polymer of about the same molecular weight as the desired maleimide product, but with two maleimidyl termini, and with regard to Table 2, "% Dimer of MAL" refers to species formed from the reaction of two functionalized PEG species to each other, % Trimer of MAL refers to species formed from the reaction of three functionalized PEG species to each other, and "% Higher MW than Timer" refers to species formed from the reaction of four or more functionalized PEG species to each other.

TABLE 1

HPLC Analyses of the Products From Examples 5 to 12

| | HPLC | | | | |
| --- | --- | --- | --- | --- | --- |
| Product from Example # | % Substitution of Maleimide | % of mPEG-Maleamic Acid | % of Unknowns + mPEG-Maleamic Acid | % of Unreacted species | % of Dimaleimidyl species |
| Example 5 | 89 | ≦1.9 | 6.8* | 4 | 3.7 |
| Example 6 | 86 | ≦1.1 | 6.6* | 7.5 | 2.6 |
| Example 7 | 89 | ≦1.9 | 4.6* | 6 | 2.5 |
| Example 8 | 88 | ≦1.4 | 3.1* | 6.3 | 2.5 |
| Example 9 (Comparative) | 83 | 7.9 | 9.7* | 5.9 | 3.8 |
| Example 10 *** (Comparative) | 0 | 65 | — | — | — |
| Example 11 (Comparative) | 86 | 4.5 | 4.5* | 7.7 | 1.8 |
| Example 12 (Comparative) | 80 | 13.6 | 14.2* | 4 | 2 |

*Includes the mPEG-maleamic peak, but not unreacted species
*** Example experienced a temperature excursion

TABLE 2

GFC and ¹H NMR Analyses of the Products From Examples 5 to 12 and
Yields and Batch Sizes of the Products From Examples 5 to 8

| Product from Example # | GFC (Gel Filtration Chromatography) | | | ¹H NMR | | Mass Yield (%) | Batch Size (g) |
|---|---|---|---|---|---|---|---|
| | % Dimer of MAL | % Trimer of MAL | % Higher MW than trimer | % of substituted maleamic acid species | % Open-ring ester impurity | | |
| Example 5 | 3.2 | 1.3 | 1.1 | 0 | 0 | 85 | ~25 |
| Example 6 | 4.5 | 1.2 | 0 | 2 | 2.3 | 88 | ~25 |
| Example 7 | 2.8 | 0.4 | 0.3 | ≦1.5** | ≦2.0** | 79 | ~25 |
| Example 8 | 2.3 | 0.4 | 0 | 0 | 0 | 85 | ~25 |
| Example 9 (Comparative) | 1.6 | 0 | 0 | 0 | 0 | 93.5 | ~1122 |
| Example 10*** (Comparative) | — | — | — | — | — | 66.4 | ~797 |
| Example 11 (Comparative) | 0.9 | 0 | 0.6 | 5.8 | 0 | 90.7 | ~463 |
| Example 12 (Comparative) | 0.7 | 0 | 0 | 0 | 0 | 87 | ~1045 |

**Not quantifiable, but value provided is the expected value
***Example experienced a temperature excursion From Table 1, it is clear that the general method employed in Examples 5 though 8 resulted in compositions having greater maleimide substitution than the composition generated in accordance with the aqueous-based approach followed in comparative Examples 9 through 12. Often, the general method employed in Examples 5 through 8 provided maleimide substitution greater than 86 percent. Also, Table 1 demonstrates the general method employed in Examples 5 though 8 resulted in compositions having a percentage of polymers bearing a maleamic acid ("mPEG-maleamic acid") of less than 4 percent, and even less than 2 percent, which is better than could be achieved with the aqueous-based approach followed in comparative Examples 9 through 12.

From Table 2, it appears that with the exception higher molecular weight species analyzed through gas filtration chromatography (% dimer of maleimide, % trimer of maleimide and other high molecular weight species), parameters such as the percentages of M-MAL 20 k precursor and open-ring ester impurity are fairly consistent among the examples tested.

Finally, it is clear from Tables 1 and 2 that the general method employed in Examples 5 though 8 provided consistent and good yields when compared to general method employed in the comparative Examples.

What is claimed is:
1. A synthetic method comprising:
a) combining a composition comprising a plurality of amine-terminated, water-soluble polymers, each amine-terminated, water-soluble polymer in the plurality encompassed by having the structure,

POLY-(X²)<sub>c</sub>—NH₂, wherein
POLY is a water-soluble polymer,
(c) is zero or one, and
X², when present, is a spacer moiety,
with a composition comprising a plurality of maleimide reagents, each maleimide reagent in the plurality encompassed by the structure,

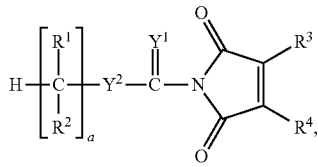

wherein
Y¹ is O or S,
Y² is O or S,
(a) is an integer from 1 to 20,
R¹, in each instance, is independently H or an organic radical,
R², in each instance, is independently H or an organic radical,
R³, in each instance, is independently H or an organic radical, and
R⁴, in each instance, is independently H or an organic radical,
under substantially nonaqueous conditions to form a composition comprising a plurality of substituted maleamic acid-terminated, water-soluble polymers, each substituted maleamic acid-terminated, water-soluble polymer in the plurality encompassed by the structure,

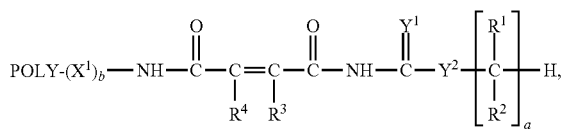

wherein
POLY is a water-soluble polymer,
(b) is zero or one,
X¹, wherein present, is a spacer moiety,
Y¹ is O or S,
Y² is O or S, (a) is an integer from 1 to 20, $R^1$, in each instance, is independently H or an organic radical, $R^2$, in each instance, is independently H or an organic radical, $R^3$, in each instance, is independently H or an organic radical, and $R^4$, in each instance, is independently H or an organic radical;

b) isolating the substituted maleamic acid-terminated, water-soluble polymer to form a polymer composition wherein at least about 90% of all polymer species in the composition are substituted maleamic acid-terminated, water-soluble polymers;

c) forming a dissolved substituted maleamic acid-terminated, water-soluble polymer composition by dissolving substituted maleamic acid-terminated, water-soluble polymers contained within the substituted maleamic acid-terminated, water-soluble polymer composition; and d) exposing the dissolved substituted maleamic acid-terminated, water-soluble polymer composition to elimination conditions to thereby result in a composition comprising a plurality of maleimide-terminated, water-soluble polymers, each maleimide-terminated, water-soluble polymer in the plurality encompassed by the structure,

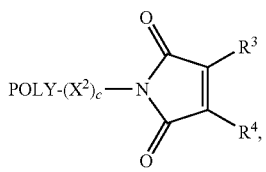

wherein,

POLY is a water-soluble polymer, (b) is zero or one, $X^1$, wherein present, is a spacer moiety, $R^3$, in each instance, is independently H or an organic radical, and $R^4$, in each instance, is independently H or an organic radical, wherein the elimination conditions comprise conditions selected from the group consisting of heating, addition of a drying agent, and combinations thereof.

2. The method of claim 1, wherein isolating the substituted maleamic acid-terminated, water-soluble polymer is effected by precipitation to form the substituted maleamic acid-terminated, water-soluble polymer composition.

3. The method of claim 2, wherein precipitation is effected by adding an excess of an agent selected from the group consisting of isopropyl alcohol, diethyl ether, MTBE, heptane, THF, hexane, and mixtures thereof.

4. The method of claim 1, carried out in an organic solvent.

5. The method of claim 4, wherein the organic solvent is selected from the group consisting of halogenated aliphatic hydrocarbons, alcohols, aromatic hydrocarbons, halogenated aromatic hydrocarbons, amides, nitriles, ketones, acetates, ethers, cyclic ethers, and combinations thereof.

6. The method of claim 4, wherein the organic solvent is selected from the group consisting of dichloromethane, chloroform, acetonitrile, toluene, methyl t-butyl ether, tetrahydrofuran, octanol, ethyl acetate, diethylcarbonate, acetone, cyclohexane and combinations thereof.

7. The method of claim 6, wherein the organic solvent is dichloromethane or acetonitrile.

8. The method of claim 1, wherein the step of combining the composition comprising a plurality of amine-terminated, water-soluble polymers with the composition comprising a plurality of maleimide reagents under substantially nonaqueous conditions to form the composition comprising a plurality of substituted maleamic acid-terminated, water-soluble polymers is carried out in the presence of basic catalyst.

9. The method of claim 1, wherein the step of exposing the dissolved substituted maleamic acid-terminated, water-soluble polymer composition to elimination conditions is carried out in an organic solvent in the presence of a base.

10. The method of claim 9, wherein the base is selected from the group consisting of sodium bicarbonate, potassium bicarbonate, sodium carbonate, or potassium carbonate.

11. The method of claim 9, wherein the step of exposing the dissolved substituted maleamic acid-terminated, water-soluble polymer composition to elimination conditions is carried out at a temperature of 10 to 60° C.

12. The method of claim 1, wherein the step of exposing the dissolved substituted maleamic acid-terminated, water-soluble polymer composition to elimination conditions is carried out in the presence of a non-nucleophilic amine catalyst.

13. The method of claim 12, wherein the non-nucleophilic amine catalyst is selected from the group consisting of diisopropylethylamine, triethylamine, n-methyl morpholine, pyridine, N,N-Dimethyl-4-aminopyridine, 1,8-Diazabicyclo[5.4.0]undec-7-ene, and 1,4-diazabicyclo[2.2.2]octane.

14. The method of claim 1, wherein the step of exposing the dissolved substituted maleamic acid-terminated, water-soluble polymer composition to elimination conditions comprises performing the step in the presence of a drying agent.

15. The method of claim 14, wherein the drying agent is selected from the group consisting of $NaHCO_3$, $Na_2CO_3$, $CaCl_2$, $CaSO_4$, $MgSO_4$, KOH, $Na_2SO_4$, $K_2CO_3$, $KHCO_3$, molecular sieves and combinations thereof.

16. The method of claim 1, wherein the water-soluble polymer is a poly(ethylene glycol).

17. The method of claim 16, wherein the poly(ethylene glycol) has a molecular weight of about 100 to about 100,000 Daltons.

18. The method of claim 1, wherein the water-soluble polymer is a linear water-soluble polymer.

19. The method of claim 1, wherein the water-soluble polymer is $CH_3O-(CH_2CH_2O)_n-CH_2CH_2$ a is one, and further wherein n is 2 to 4000.

20. The method of claim 1, wherein the water-soluble polymer is branched.

21. The method of claim 1, wherein the substantially nonaqueous conditions represents a reaction medium having less than 1000 parts per million of water.

22. The method of claim 21, wherein the substantially nonaqueous conditions represents a reaction medium having less than 100 parts per million of water.

23. The method of claim 22, wherein the substantially nonaqueous conditions represents a reaction medium having less than 60 parts per million of water.

* * * * *